(12) United States Patent
Schröder

(10) Patent No.: US 7,659,730 B2
(45) Date of Patent: Feb. 9, 2010

(54) MEASURING APPARATUS AND METHOD FOR RECOGNIZING FOREIGN BODIES IN A PRODUCT, PARTICULARLY TOBACCO, COTTON OR ANOTHER FIBROUS PRODUCT

(75) Inventor: Dierk Schröder, Hamburg (DE)

(73) Assignee: Hauni Maschinenbau Ag, Hamburg (DE)

(*) Notice: Subject to any disclaimer, the term of this patent is extended or adjusted under 35 U.S.C. 154(b) by 184 days.

(21) Appl. No.: 11/793,948

(22) PCT Filed: Dec. 17, 2005

(86) PCT No.: PCT/EP2005/013830

§ 371 (c)(1),
(2), (4) Date: Jun. 21, 2007

(87) PCT Pub. No.: WO2006/069720

PCT Pub. Date: Jul. 6, 2006

(65) Prior Publication Data

US 2008/0084220 A1  Apr. 10, 2008

(30) Foreign Application Priority Data

Dec. 22, 2004  (DE) .................. 10 2004 063 229

(51) Int. Cl.
*G01R 27/26* (2006.01)
(52) U.S. Cl. .................. 324/658; 324/665; 356/238.1; 356/238.3
(58) Field of Classification Search .................. 324/658
See application file for complete search history.

(56) References Cited

U.S. PATENT DOCUMENTS 3,786,349 A * 1/1974 Devenyi .................. 324/658

(Continued)

FOREIGN PATENT DOCUMENTS

DE  25 00 299 A1  9/1975

(Continued)

OTHER PUBLICATIONS

German Patent and Trademark Office Examination Report, dated Oct. 19, 2005.

(Continued)

*Primary Examiner*—Timothy J Dole
*Assistant Examiner*—Benjamin M Baldridge
(74) *Attorney, Agent, or Firm*—Venable LLP; Robert Kinberg; Steven J. Schwarz

(57) ABSTRACT

The invention concerns a measuring apparatus for the detection of foreign bodies in a product, in particular in tobacco, cotton or some other fibrous product, having a measuring device, a device for generating an alternating electromagnetic field in the measuring device, which is influenced by a product which is arranged in a measuring volume of the measuring apparatus, a circuit device which includes the measuring device and which is designed to determine at least one suitable measurable variable of the alternating field influenced by the product, and an evaluating device which is designed for detection of the foreign body by suitable evaluation of the measurable variable determined with the circuit device, and is distinguished in that the measuring device is a measuring capacitor and the frequency of the alternating field is in the high-frequency range below the microwave range. The application further concerns a corresponding measuring method.

33 Claims, 6 Drawing Sheets

U.S. PATENT DOCUMENTS

Figure 1:
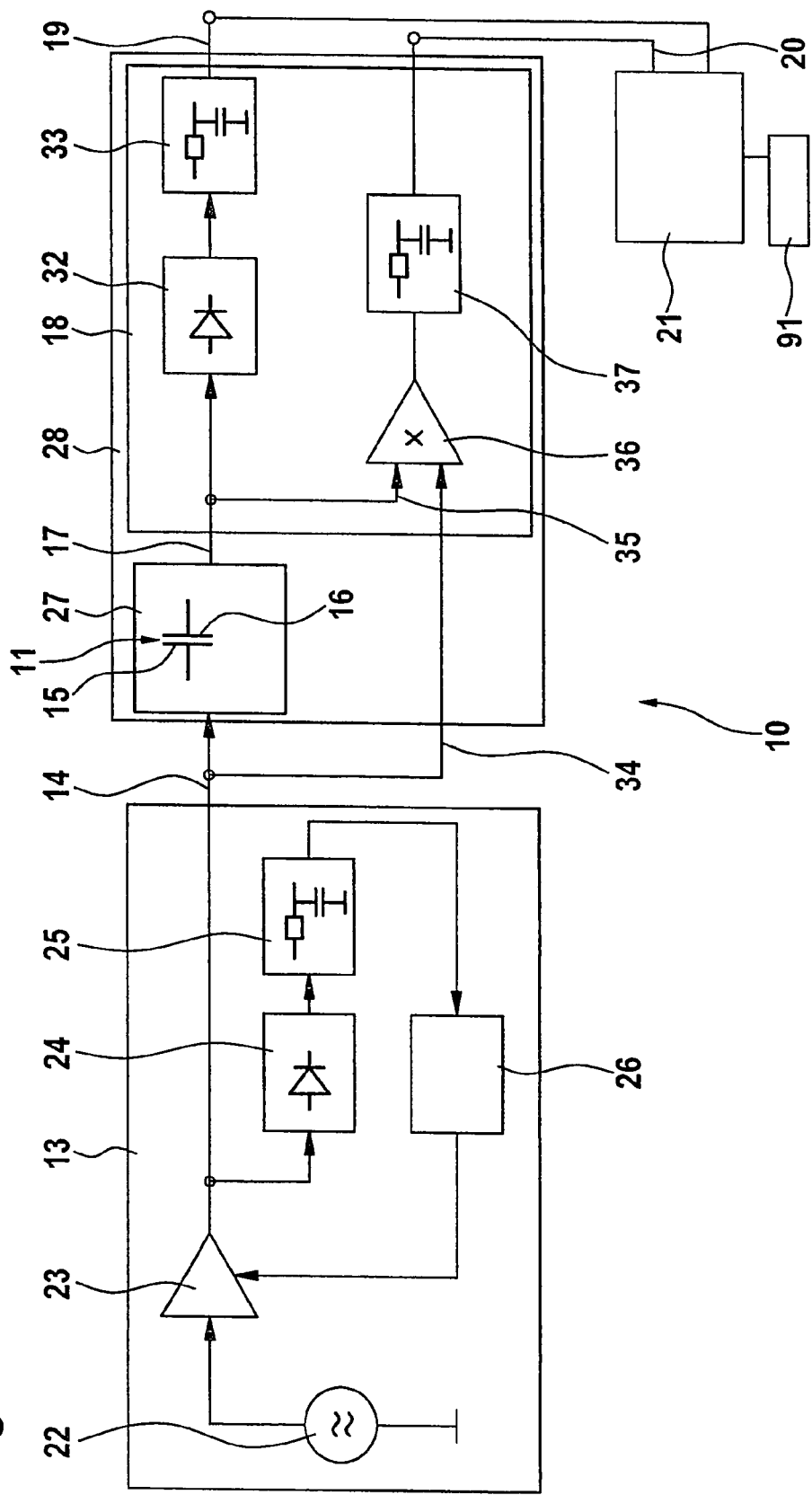

| | | | |
|---|---|---|---|
| 3,979,581 A | | 9/1976 | Reuland |
| 3,996,942 A | * | 12/1976 | Baier ........................ 131/280 |
| 4,114,090 A | | 9/1978 | Poskitt |
| 4,505,186 A | * | 3/1985 | Meier et al. ................... 92/5 R |
| 4,947,131 A | * | 8/1990 | Mayer et al. ................ 324/671 |
| 5,208,544 A | * | 5/1993 | McBrearty et al. .......... 324/687 |
| 5,302,907 A | * | 4/1994 | Hohenstein et al. ......... 324/655 |
| 6,073,480 A | * | 6/2000 | Gokhfeld .................... 73/29.02 |
| 6,346,819 B1 | * | 2/2002 | Joss et al. ................... 324/665 |
| 6,768,317 B2 | | 7/2004 | Moller et al. |
| 2003/0020494 A1 | * | 1/2003 | Desmier et al. ............. 324/667 |
| 2003/0107729 A1 | * | 6/2003 | Furter ..................... 356/238.1 |
| 2008/0164887 A1 | | 7/2008 | Schröder |

FOREIGN PATENT DOCUMENTS

| | | |
|---|---|---|
| DE | 24 41 832 A1 | 3/1976 |
| DE | 27 00 972 C3 | 6/1980 |
| DE | 37 43 216 A1 | 6/1989 |
| DE | 38 25 111 A1 | 1/1990 |
| DE | 196 51 355 A1 | 6/1998 |
| DE | 100 37 180 C1 | 1/2002 |
| DE | 101 00 664 A1 | 7/2002 |
| EP | 902 277 A1 | 7/1998 |
| EP | 0 924 513 A1 | 6/1999 |
| EP | 1 327 876 B1 | 7/2003 |
| EP | 1 330 961 A1 | 7/2003 |
| FR | 1315918 | 1/1963 |
| GB | 717127 | 10/1954 |
| GB | 1 132 763 A | 11/1968 |

OTHER PUBLICATIONS

International Search Report dated Jun. 13, 2006, issued in PCT/EP2005/013830.

Examination Report dated Oct. 19, 2005, issued in DE 10 2004 063 229.4.

Caranti G M et al: "A Vector Impedance Meter Digitally Controlled" Review of Scientific Instruments, AIP, Melville, NY, US, vol. 62, No. 12, Dec. 1, 1991, pp. 3092-3097, XP000278580.

Smit Q et al: "General purpose self-tuning capacitance sensor [for oil] recycling and soil moisture measurement application" IMTC/98 Conference Proceedings. IEEE Instrumentation and Measurement Technology Conference. Where Instrumentation is Going (Cat. No. 98CH36222) IEEE New York, NY, USA, vol. 2, 1998, pp. 1074-1078, XP010281750.

Huang S M et al: "Electronic transducers for industrial measurement of low value capacitances" Journal of Physics E (Scientific Instruments) vol. 21, No. 3, Mar. 1988, pp. 242-250.

Iacopini E et al: "Digital techniques applied to phase-sensitive detection" Journal of Physics E (Scientific Instruments) vol. 16, No. 9, Sep. 1983, pp. 844-847, XP020017183.

Saniie J et al: "Digital phase detection based on in-phase and quadrature sampling" Journal of Physics E. Scientific Instruments, IOP Publishing, Bristol, vol. 16, No. 7, Jul. 1, 1983 pp. 606-607, XP020017126.

International Search Report dated Jul. 19, 2006, issued in PCT/EP2005/013831.

Non Final Office Action issued in related U.S. Appl. No. 11/793,947, dated Mar. 6, 2009.

German Patent and Trademark Office Examination Report, dated Oct. 19, 2005.

* cited by examiner

MEASURING APPARATUS AND METHOD FOR RECOGNIZING FOREIGN BODIES IN A PRODUCT, PARTICULARLY TOBACCO, COTTON OR ANOTHER FIBROUS PRODUCT

CROSS REFERENCE TO RELATED APPLICATIONS

This application is a national stage of International Application No. PCT/EP 2005/013830, filed Dec. 17, 2005, and claims priority to German Application No. 10 2004 063 229.4, filed Dec. 22, 2004, the entire contents of each of which are incorporated herein by reference.

The invention concerns a measuring apparatus for the detection of foreign bodies in a product, in particular in tobacco, cotton or some other fibrous product, according to the preamble of claim 1. The invention further concerns a corresponding measuring method.

For the detection of foreign bodies in tobacco, the use of microwave measuring apparatuses is known from documents DE 100 37 180 C1, DE 101 00 664 A1, EP 1 327 876 B1, EP 1 330 961 A1, for example. On account of the required high precision of measurement and the high frequencies used, the circuitry is highly elaborate.

It is the object of the present invention to provide a structurally simple measuring apparatus for the detection of foreign bodies with high precision of measurement.

The invention achieves this object with the features of claims 1 and 28. By using a capacitor, in particular instead of a microwave resonator, and a high-frequency field below the microwave range, the circuitry can be made significantly less elaborate. Also, under certain circumstances by means of a capacitor a more homogeneous field can be generated in the product chamber than by means of a microwave resonator, in which the electric field strength disappears at the peripheral wall.

The term "foreign body" means any material of a different kind which is undesirably also present in the two-medium system to be tested. The two-medium system to be tested is formed in particular by product and moisture (or casing), or filter material and glycerine triacetate. The invention differs in this from known capacitive measuring apparatuses in the high-frequency range for the detection of mass or density faults, for example in tobacco, which concern only the two-component system of product and moisture. Due to its different dielectric properties, in a certain way a foreign body influences the high-frequency field and therefore the determined measurable variables. By suitable evaluation in the evaluating device, a foreign body in the product can be detected from the determined measurable variables, particularly if the curve of a measurable variable shows a deviation caused by the foreign body.

The term "high frequency" means basically, as differentiated from the microwave range, fields having a frequency below 100 MHz, preferably below 10 MHz. As a rule, the frequency is more than 10 kHz or more than 100 kHz. In a preferred variant of the invention, a high-frequency field with a frequency below 5 MHz, preferably below 1 MHz, is used. This is surprising because it is known with regard to the measurement of moisture and/or density of the product that an accurate enough measurement is possible only within an increasingly limited measuring range towards lower frequencies, so that for example for tobacco a measuring frequency of at least 5 MHz is deemed appropriate. For determining foreign bodies particularly in tobacco, cotton and other fibrous products, however, it is precisely at lower frequencies that greater sensitivity of measurement occurs. An explanation for this is that at lower frequencies macroscopic conduction has an increasing influence, but this is not true of typical non-conducting foreign-body materials (or, more generally, those with different macroscopic conductivity), so that the difference in the dielectric constants between product and foreign body is greater in the measuring range of the invention than in the microwave range.

As a result of the preferred use of a travelling high-frequency wave and a substantially non-resonant circuit device in which the measuring capacitor is therefore not a frequency-determining part of a measuring oscillating circuit, the use of an oscillating circuit coil sensitive to temperature effects can be dispensed with. "Substantially" means that resonant field components are not excluded as long as the principle of measurement is essentially based on a progressive wave. Since no resonance condition has to be fulfilled for a measuring oscillating circuit, the measuring capacitor can have a lower capacitance than in the state of the art, preferably less than 10 pF, which reduces the elaborateness and size. The preferred embodiment described therefore differs from known capacitive measuring devices in the high-frequency range for the detection of mass or density faults in tobacco, in which a measuring capacitor and a coil are connected as frequency-determining parts in a high-frequency oscillating circuit, wherein the resonant frequency and resonant amplitude of the high-frequency field, which are affected by the product, are determined as measurable variables, for example.

Preferably, the detection of foreign bodies is based on the fact that two independent measurable variables, in particular one measurable variable dependent on the capacitance of the measuring capacitor and one measurable variable dependent on the loss factor of the measuring capacitor, are in a ratio different to the expected curve. Preferably the measurement of two independent measurable variables is therefore provided. Advantageously, in this case two measurable variables dependent on the amplitude and the phase of the high-frequency wave are determined. Basically, therefore, the generation of a high-frequency wave is sufficient, which reduces the elaborateness compared with those apparatuses which are based on the use of several high-frequency waves having different high frequencies. However, it is not essential to determine two independent measurable variables; it is also conceivable to perform detection of foreign bodies from the curve of only one measurable variable.

The part of the circuit device which serves to determine the measurable variables is as a rule connected to the output of the actual measuring circuit which includes the measuring capacitor. While the measuring circuit as a rule has one output for the high-frequency field influenced by the product, the device for determining the measurable variables as a rule has a number of outputs corresponding to the number of measurable variables to be determined, preferably therefore two outputs. It is also possible for the measuring circuit and the device for determining the measurable variables to form a unit. The device for determining the measurable variables is connected to the input of the actual evaluating device for the detection of foreign bodies by evaluating the measuring signal. It is also possible for the device for determining the measurable variables and the evaluating device to form a unit.

In a preferred embodiment, the part of the circuit device which serves to determine the measurable variable or variables is constructed with digital electronics. This enables the use of simple methods for determining the desired measurable variable, for example, the capacitive fraction and the loss fraction of the output voltage value of the measuring circuit.

A particularly simple and therefore preferred method is based on the orthogonality of the sine and cosine fractions and includes the measurement of a discrete number of n measured values, for example, voltage values, over each oscillation period of the high-frequency field, separate multiplication of the n measured values by corresponding sine and cosine values, and separate addition of these sine and cosine products. The totals obtained constitute the measurable variables or can be further processed to determine the measurable variables.

A particularly simple form of a measuring circuit, i.e. part of the circuit device including the measuring capacitor, is an RC network, preferably with an operational amplifier. This preferably involves an RC differentiating network, but an RC integrating network may also be used, for example.

In a preferred embodiment, parts of the sensor are made of a material with a low temperature expansion coefficient in order to keep the effects of temperature fluctuations on the precision of measurement as low as possible. For the same purpose the sensor can have an additional device for keeping the temperature of the measuring capacitor constant. An additional device for measuring the temperature of the measuring capacitor, for example, a temperature sensor, is also conceivable in order to be able to correct the measuring signal accordingly.

Preferably the capacitor is arranged essentially perpendicular to the direction of transport of the product. With a plate capacitor, therefore, the capacitor plates are arranged perpendicularly to the direction of transport. This makes it possible to arrange the electrodes a short distance from each other, for example, less than the thickness of the endless product rod. This can result in improved resolution with respect to the detection of foreign bodies in the longitudinal direction, and hence an increase in sensitivity of detection.

The sensor is designed to feed the product through the space formed between the electrodes of the measuring capacitor, to allow detection of the product as completely and uniformly as possible. A leakage field sensor is therefore preferably not involved.

Another preferred embodiment concerns the measurement of a relatively broad product, for example, a tobacco or tow web or a cotton layer fleece, or a plurality of endless product rods located beside each other. In this case the sensor includes a plurality of measuring capacitors arranged across the width of the product. This arrangement permits lateral position-finding of a detected foreign body in a simple manner. The electrodes connected to the high-frequency field-generating device are kept at the same potential, for example, simply short-circuited, to minimise crosstalk between the measuring capacitors. For the same purpose the other electrodes are preferably also in each case kept virtually at the same potential by means of inverting operational amplifiers.

Figure 2:
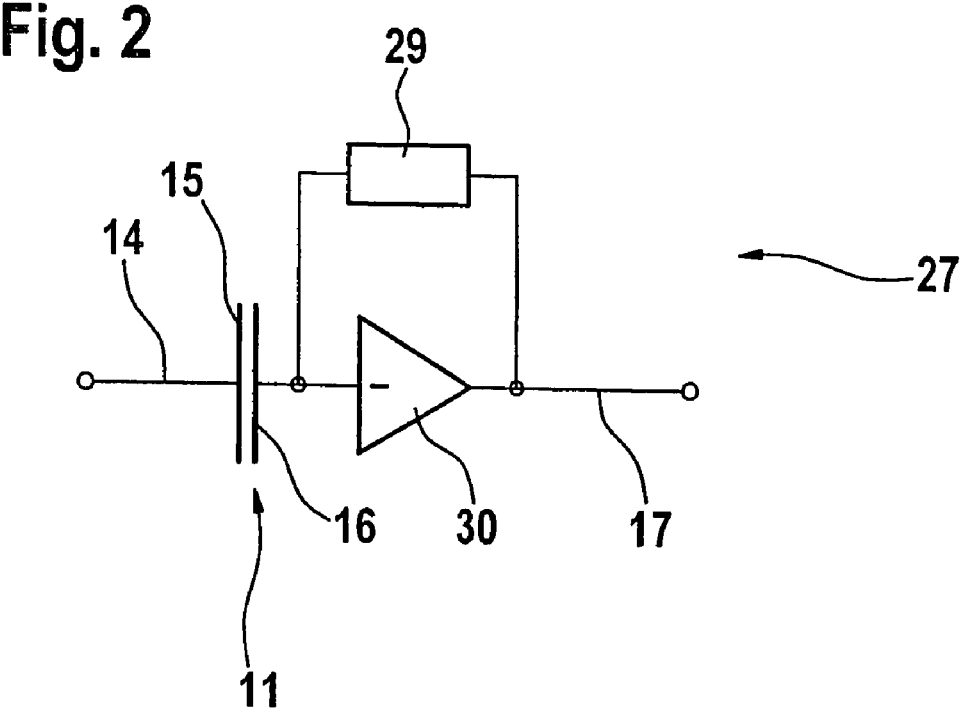
Figure 3:
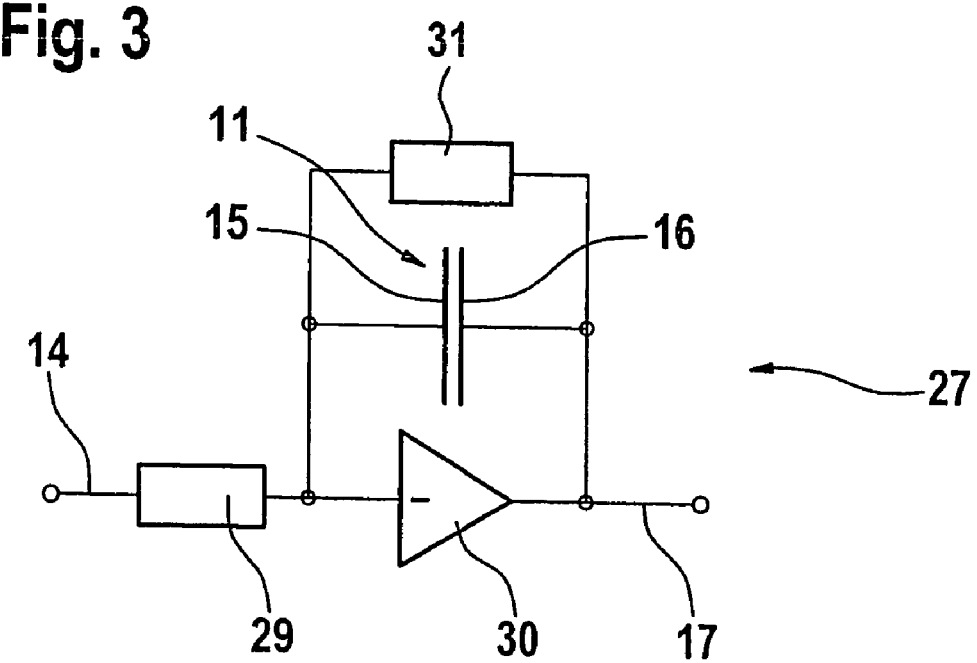
Figure 4:
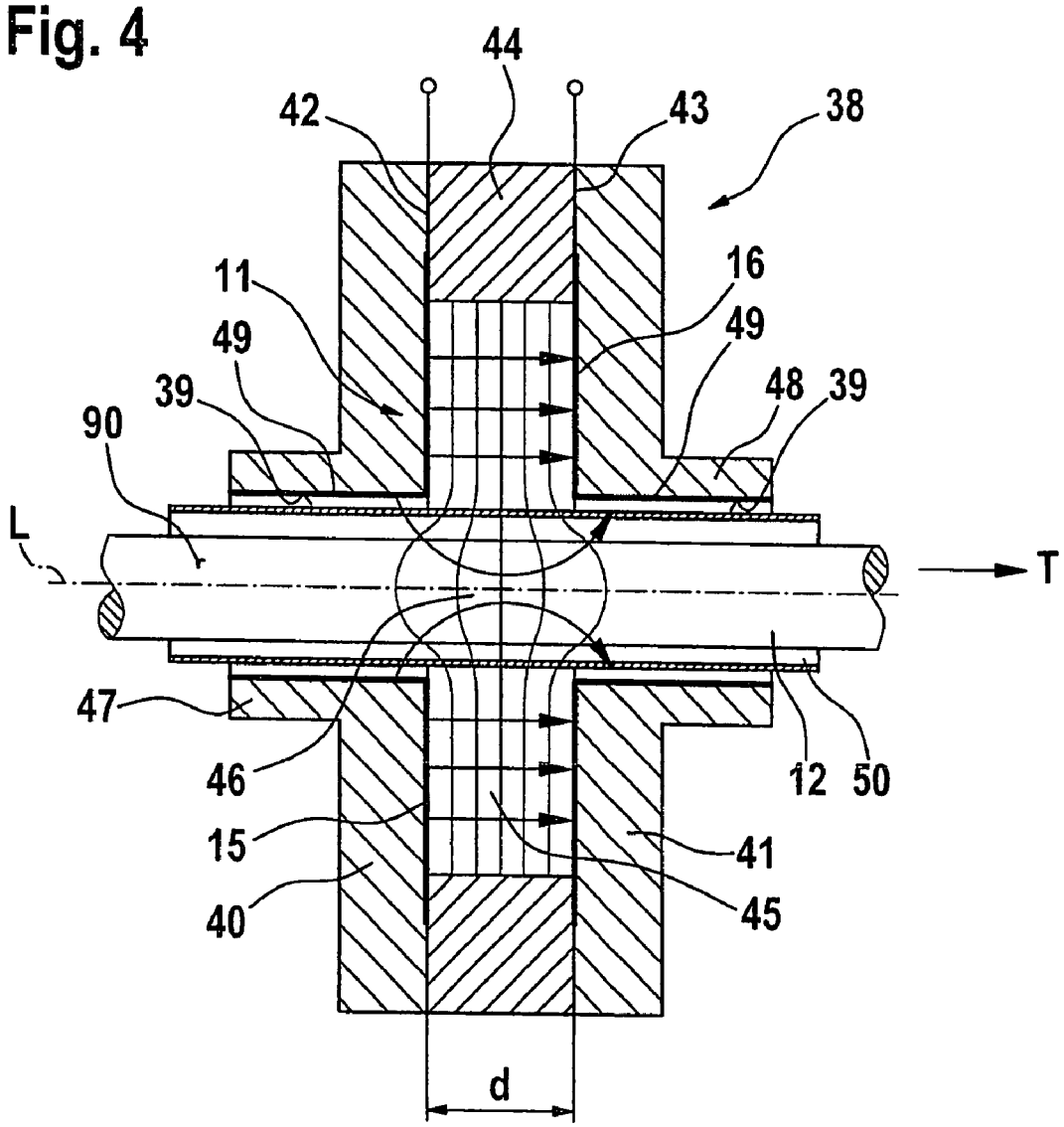
Figure 5:
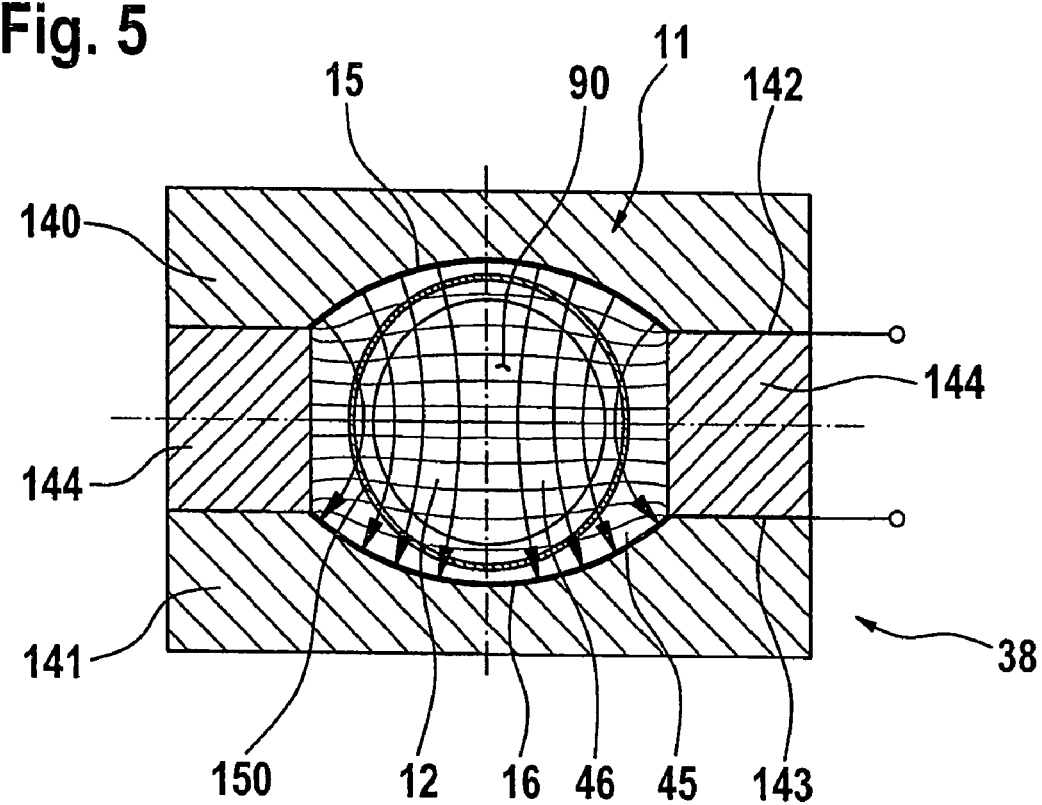
Figure 6:
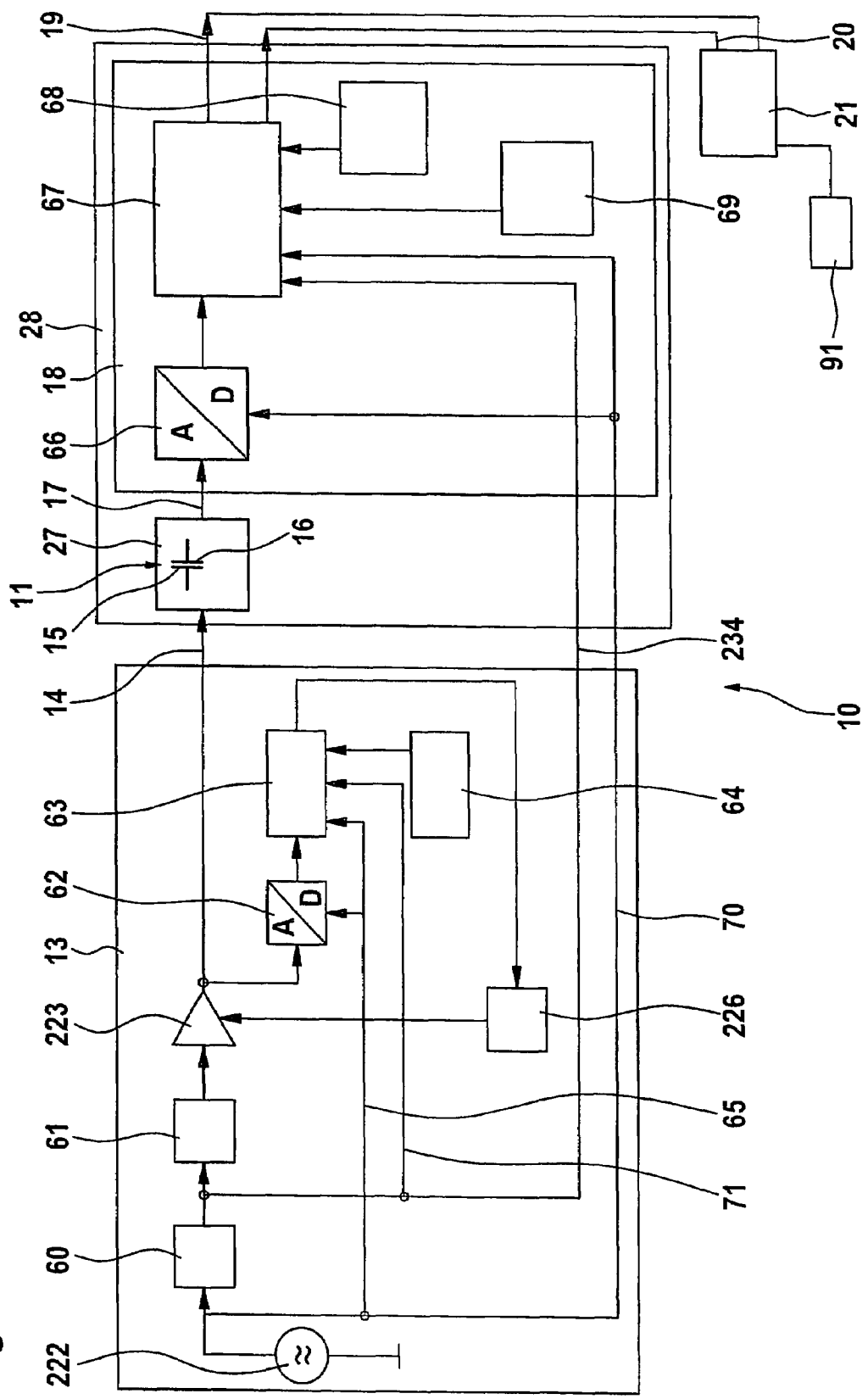
Figure 7:
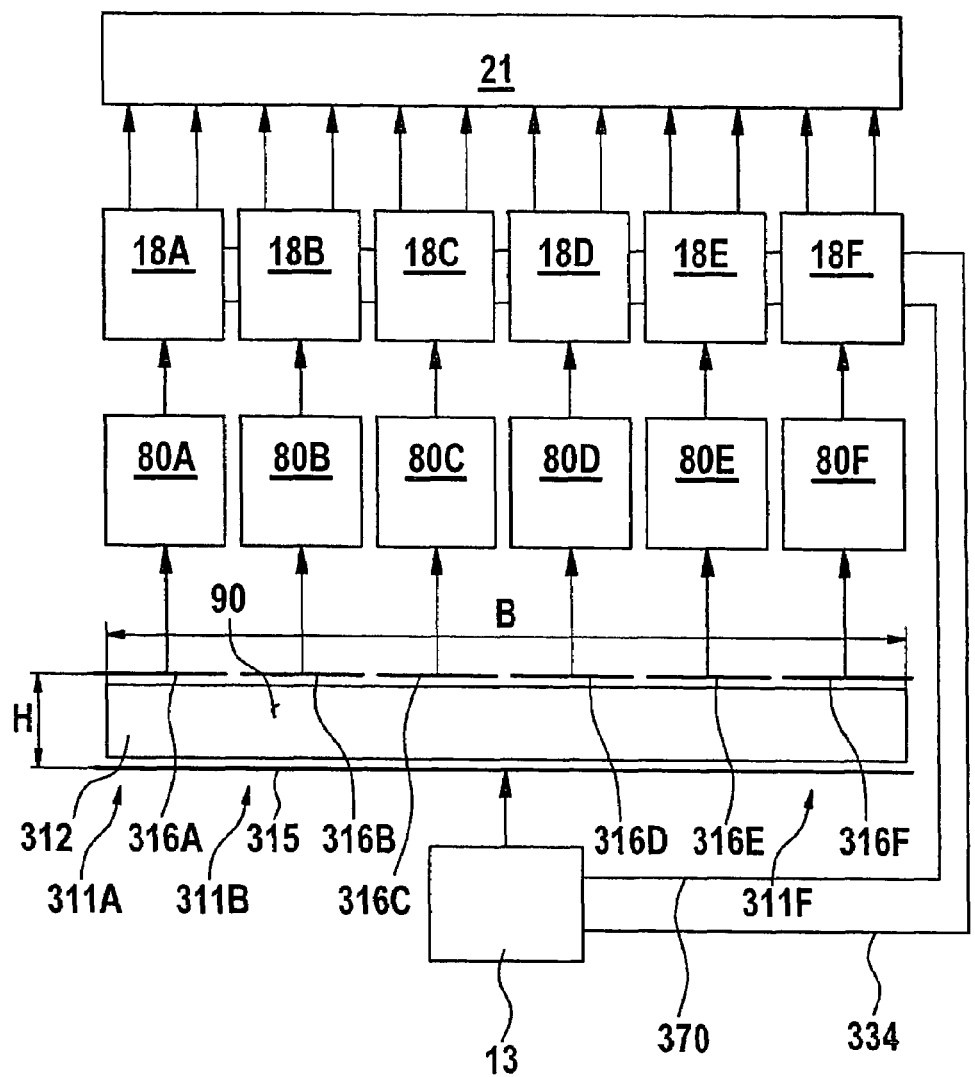
Figure 8:
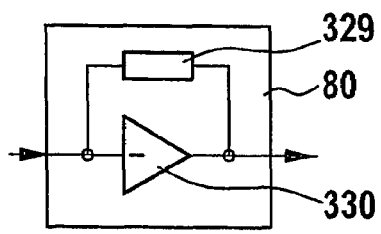

Further advantageous features are apparent from the subsidiary claims and the description of advantageous embodiments with reference to the attached drawings. They show:

FIG. 1: a schematic circuit of an essentially analogue measuring apparatus;

FIG. 2: a differentiating measuring circuit for a measuring apparatus;

FIG. 3: an integrating measuring circuit for a measuring apparatus;

FIG. 4: a longitudinal sectional view of a capacitive sensor;

FIG. 5: a cross-sectional view of a capacitive sensor in a further embodiment;

FIG. 6: a schematic circuit of an essentially digital measuring apparatus;

FIG. 7: a schematic circuit of a measuring apparatus for measurement on a wide product; and FIG. 8: an operational amplifier for a differentiating measuring circuit for the measuring apparatus from FIG. 7.

The capacitive measuring apparatus 10 according to FIGS. 1 to 6 includes a high frequency generating device 13 for generating a high-frequency wave which is supplied via an input wire 14 to a circuit device 28. The circuit device 28 includes a measuring capacitor 11 through which is passed the product 12 to be measured, which is in the form of an endless rod in the present case. The high-frequency wave generated by the high frequency generating device 13 is passed to an electrode 15 of the measuring capacitor 11 in order to generate in it a high-frequency field which interacts with the product 12. The high-frequency wave emanating from the other electrode 16 of the measuring capacitor 11 and influenced by the product 12 is processed by means of the circuit device 28 in order to determine at least one, preferably two measurable variables independent of each other and dependent on the amplitude and/or the phase of the high-frequency wave influenced by the product 12. These are preferably two measurable variables dependent on the capacitance and the loss factor of the measuring capacitor 11. Measuring signals corresponding to the measurable variables are passed to the evaluating device 21, for example a suitably programmed computer.

In the product 12 an unwanted foreign body 90 can occur, for example a plastic or metal particle. On account of different dielectric properties, in a given manner the foreign body 90 determines the amplitude and phase of the high-frequency wave and hence also the determined measurable variables. By suitable evaluation in the evaluating device 21, a foreign body 90 in the product 12 can be detected from the measurable variables determined, particularly if the curve of a measurable variable shows a deviation caused by the foreign body 90. For instance, spikes in a measuring curve can be caused by a foreign body 90; the evaluating device is then appropriately designed for the detection of such spikes in the measuring curve. The evaluation of the ratio of two measurable variables independent of each other is tried and tested for the detection of foreign bodies. The evaluating device 21 can if necessary control a removal means 91, for example, a blow nozzle, for removing part of the product 12 in which a foreign body 90 is detected.

The embodiment according to FIG. 1 concerns an essentially analogue measuring apparatus. The high frequency generating device 13 includes a harmonic oscillator 22 for generating a high-frequency wave. The voltage amplitude $U_e$ of the generated high-frequency wave is preferably kept constant by means of a regulating device 23-26 in order to allow measurement uninfluenced by fluctuations of input amplitude. For this purpose the high-frequency wave generated by the harmonic oscillator 22 is supplied to a controllable amplifier 23. The output signal of the amplifier 23 is supplied to a rectifier 24 whose output signal is passed on via the low-pass filter 25 to a controller 26. The controller 26 controls the amplifier 23 in such a way that the amplitude $U_e$ of the harmonic oscillation at the output of the amplifier 23 has a constant value.

The measuring circuit 27 is the part of the circuit device 28 directly connected to the measuring capacitor 11. Any measuring circuit which is designed to generate an adequate amplitude and phase variation of the high-frequency wave as a result of the product 12 passing through the measuring capacitor 11 is suitable here. Two preferred embodiments of the measuring circuit 27 are shown in FIGS. 2 and 3, wherein the measuring capacitor 11, a resistor 29 and an inverting operational amplifier 30 are connected in a differentiating arrangement according to FIG. 2 or an integrating arrangement as in FIG. 3. The non-inverting input of the operational amplifier 30 is appropriately grounded. With the integrating arrangement according to FIG. 3, an additional resistor 31 is provided to prevent, if necessary, the output signal from breaking into oscillation .The output signal of the measuring circuit 27 which corresponds to the outgoing high-frequency wave undergoes, due to interaction with the product 12, a voltage amplitude $U_a$ which is altered from the input amplitude $U_e$, as well as a phase shift compared with the input signal.

The high-frequency wave passing through the measuring capacitor 11 is passed via the output wire 17 of the measuring circuit 27 to the device 18 for determining the measurable variables. The device 18 for determining the measurable variables determines suitable measurable variables from the high-frequency signal. For this purpose, in the embodiment according to FIG. 1 the output signal of the measuring circuit 27 is delivered to a rectifier 32 and smoothed in a low-pass filter 33. The signal obtained in this way is proportional to the output amplitude $U_a$. Furthermore, the input signal generated by the high frequency generating device 13 is delivered via the wire 34 to the device 18 for determining the measurable variables. In general, advantageously a signal dependent on the high-frequency wave generated is passed to the circuit device 28 via a wire 34, 234 provided in addition to the measuring wire via the measuring capacitor 11, in order to be able to use the phase information of the input signal for determining the phase shift of the output signal. In the present case the input signal of the measuring capacitor 11 is passed via the wire 34 and the output signal of the measuring capacitor 11 or the measuring circuit 27 is passed via a wire 35 to the multiplication amplifier 36, in which they are multiplied by each other and smoothed with a low-pass filter 37. The signal obtained in this way is proportional to the output amplitude $U_a$ times the sine (or cosine) of the phase shift. From the curve of the measurable variables determined by means of the device 18 for determining the measurable variables, in particular from a correspondingly formed ratio, and comparison with a curve to be expected, any foreign bodies 90 contained in the product can be detected if a deviation is found. For corresponding evaluation, the measuring signals are passed via the output wires 19, 20 to the evaluating device 21 in which evaluation is carried out by means of a computer program stored therein, for example.

A preferred embodiment of a high-frequency sensor 38 is shown in FIG. 4. The sensor 38 is constructed substantially rotationally symmetrically about the longitudinal axis L. Through a central longitudinal bore 39 of the sensor 38 the endless product rod 12, for example, an endless tobacco rod, is passed in the direction of transport T which coincides with the longitudinal direction L. The sensor includes two rotationally symmetrical, disc-shaped base bodies 40, 41 which are oriented perpendicularly to the longitudinal direction L and which are spaced apart from each other by means of an outer, annular, non-conductive boundary body 44 and which each comprise a central through-hole 39 for the endless product rod. To each of the inner surfaces of the base bodies 40, 41 oriented perpendicularly to the longitudinal direction L is applied an electrode 15, 16 of the measuring capacitor 11 in the form of a metal surface, for example a metal coating, for example by vapour deposition of gold. The measuring capacitor 11 is therefore designed as a plate capacitor with plate-like electrodes 15, 16 which are disc-shaped and oriented perpendicularly to the longitudinal direction L and comprise a central through-hole for the endless product rod 12. In this arrangement the field lines run substantially parallel to the direction of transport. Between the base bodies 40, 41 is formed a field-filled space 45 which is radially closed off from the outside by the boundary body 44. The high-frequency field extends into the central product space 46 and there interacts with the product 12. The plates 15, 16 have a shorter radius than the base bodies 40, 41 in order to prevent emergence of the high-frequency field into the environment of the sensor. The plates 15, 16 of the plate capacitor 11 can be arranged a short distance d from each other to improve the measuring resolution in the longitudinal direction L. The distance d can be in particular shorter than the diameter of the endless product rod 12 and, for example, less than 8 mm, preferably less than 4 mm. Conductive connections 42, 43 between the electrodes 15, 16 and external electrical terminals are also provided. The base bodies 40, 41 each have a tubular, axially outwardly extending extension 47, 48 encompassing the endless product rod. The extensions 47, 48 have a metal surface or coating 49 on the inner wall, which is appropriately connected to the electrodes 15, 16. The metal coating 49 forms a metal chimney to prevent leaking of the field from the product through-holes in the capacitor 11. Furthermore, a tube 50 of non-conductive material directly surrounding and guiding the endless product rod 12 and extending over the whole length of the sensor is provided, which prevents contamination of the interior of the sensor by product residues. In a further embodiment the field-filled space 45 formed between the electrodes 15, 16 can be partially or completely filled with a dielectric material, apart from the product space, for positively influencing the field pattern.

The bodies 40, 41, 44 of the sensor 38 are preferably made of a non-conductive material with a very low temperature expansion coefficient, for example, Zerodur, in order to achieve increased dimensional stability of the sensor 38 to temperature effects. On account of the reduced dependence of the capacitance properties of the measuring capacitor 11 on the ambient temperature, improved precision of measurement can be achieved. For the same purpose, preferably a regulating device, not shown, is provided for keeping the sensor temperature constant. It is also conceivable that the base bodies 40, 41 of the sensor 38 are partially or completely made of metal.

Another embodiment of a sensor 38 is shown in FIG. 5, parts corresponding to each other being denoted by corresponding reference numbers in the 100s. The electrodes 15, 16 are formed by plates which are arranged parallel to the direction of transport which is oriented perpendicularly to the plane of the paper. The field lines run in this example substantially perpendicular to the direction of transport. The plates 15, 16 are preferably arranged round the endless product rod 12 and for this purpose are preferably curved.

A preferred embodiment of a measuring apparatus 10 is shown in FIG. 6, parts corresponding to each other being denoted by corresponding reference numbers in the 200s. Unlike the embodiment according to FIG. 1, in particular the device 18 for determining the measurable variables is constructed with digital electronics. For this purpose the device 18 for determining the measurable variables has an A/D converter 66 to which is passed the measuring signal emitted by the measuring circuit 27. The A/D converter 66 is clock-controlled with a scanning frequency which is higher by a factor of n than the frequency of the high-frequency wave, n being a natural number greater than 1. The clock signal for the A/D converter 66 is generated by means of the quartz oscillator 222 in the form of a square-wave signal with a frequency of for example 50 MHz, so that in the present example n=10.

In general, therefore, the measuring apparatus 10 has a device 222 for generating a scanning signal with a scanning frequency which is higher by a factor of n than the frequency of the high-frequency wave. The scanning signal is passed via the wire 70 to the A/D converter 66.

The measured values scanned with the A/D converter 66 are passed to the digital processing device 67 which is programmed to determine suitable measurable variables independent of each other. In a preferred method for determining the measurable variables, each scanned measurement is multiplied on the one hand by the corresponding value of sine function and on the other hand by the corresponding value of cosine function. For this purpose the scanning signal is passed via the wire 70 to the processing device 67. The sine and cosine values can for example be taken from corresponding tabular memories 68, 69. The n sine values and n cosine values obtained in this way are then added up separately over a period of the high-frequency field, so that two totals are obtained. For this purpose the high-frequency input signal is passed via the wire 234 to the processing device 67, so that the latter works in phase with the high frequency generating device 13. From the totals obtained can be clearly determined, on the basis of given orthogonality relationships, the two desired measurable variables dependent on the amplitude and the phase of the measuring signal influenced by the product 12. For corresponding evaluation, the measuring signals are passed via the output wires 19, 20 to the evaluating device 21 in which evaluation is carried out for example by means of a computer program stored therein.

Advantageously, the signal generated by the high-frequency source 222 can also be used to generate the high-frequency wave used for measurement. For this purpose the signal generated by the high-frequency source 222 can be divided with the divider stage 60 by a factor of n down to a square wave of synchronous phase having a measuring frequency of 5 MHz in the present case, and then converted with the PLL circuit 61 to a sinusoidal signal of synchronous phase with the same frequency.

The control device 223, 62-64, 226 for keeping constant the voltage amplitude $U_e$ of the high-frequency wave emitted by the amplifier 223 can also be constructed with digital electronics. In this case the output signal of the amplifier 223 is supplied to an A/D converter 62 which is controlled via a wire 65 with the scanning signal of 50 MHz, as a result of which n scanned values of the signal emitted by the amplifier 223 are generated to each period. The measured values scanned with the A/D converter 62 are passed to the digital processing device 63. With a preferred method, each scanned voltage value is multiplied by the corresponding value of cosine function. For this purpose the scanning signal is passed via the wire 65 to the processing device 63. The cosine values can for example be taken from a corresponding tabular memory 64. The n cosine values obtained in this way are then added up over a period of the high-frequency field. For this purpose the high-frequency input signal is passed via a wire 71 to the processing device 63, so that the latter works in phase with the high frequency generating device 13. The output signal of the processing device 63 is forwarded to the controller 226 which controls the amplifier 223 in such a way that the output signal of the processing device 63 and hence the amplitude $U_e$ of the oscillation at the output of the amplifier 223 has a constant value.

The embodiment according to FIG. 7 serves in particular for measurement on a wide, web-like product 312, for example, a tobacco web, a tow web or an evenly spread cotton layer, whose width B is substantially greater, for example at least by a factor of 3, than its height H. Another application concerns measurement on a plurality of endless product rods located adjacent to each other, for example, endless tobacco rods. In FIG. 7 the direction of transport runs perpendicularly to the plane of the paper. Parts corresponding to each other are denoted by corresponding reference numbers in the 300s. In this embodiment a plurality of measuring capacitors 311A, 311B, . . . are used, here six for example, which are arranged across the width of the product. This arrangement allows determination of the lateral position of a foreign body or, in the case of a plurality of endless product rods located adjacent to each other, the endless product rod containing the foreign body. The measuring capacitors 311A, 311B, . . . are appropriately supplied by the same high frequency generating device 13. Preferably, all the input electrodes 315 of the measuring capacitors 311A, 311B, . . . are at the same potential, at its simplest by short-circuiting the electrodes, as shown in FIG. 7. This minimises crosstalk between the measuring capacitors 311A, 311B, . . . . The output electrode 316A, 316B, . . . of each measuring capacitor 311A, 311B, . . . is connected to a measuring circuit 80A, 80B, . . . The measuring circuit 80A, 80B, . . . is preferably constructed as shown in FIG. 8 and then forms, together with the respective measuring capacitor 311A, 311B, . . . , a differentiating measuring circuit 27 as shown in FIG. 2. The use of one inverting operational amplifier 330 each, connected to the output of the measuring capacitor 311A, 311B, . . . is particularly advantageous in this embodiment, because as a result thereof the output electrodes 316A, 316B, . . . of all the measuring capacitors 311A, 311B, . . . are virtually at the same potential, particularly grounded. This minimises crosstalk between the measuring capacitors 311A, 311B, . . . The output of each measuring circuit 80A, 80B, . . . is appropriately connected to a device 18A, 18B, . . . for determining the measurable variables, which can be constructed in particular with digital electronics, for example, as shown in FIG. 6. The devices 18A, 18B, . . . for determining the measurable variables are appropriately connected to the evaluating device 21 for the detection of foreign bodies. The corresponding methods for determining the measurable variables and for the detection of foreign bodies are preferably carried out as described above.

The invention claimed is:

1. Measuring apparatus for the detection of foreign bodies in a tobacco, cotton or other fibrous product, comprising:
    a measuring device comprising a measuring capacitor,
    a device for generating an input signal for generating an alternating electromagnetic field in the measuring device, the alternating electromagnetic field being in the high-frequency range below the microwave range, wherein the alternating electromagnetic field is influenced by a product which is arranged in a measuring volume of the measuring apparatus,
    a circuit device that determines at least one suitable measurable variable of the alternating field influenced by the product, the circuit device comprising the measuring capacitor, a rectifier receiving an output signal from the measuring capacitor, and a multiplication amplifier receiving the input signal and the output signal, and
    an evaluating device that detects the foreign body by suitable evaluation of the measurable variable determined with the circuit device.

2. Measuring method according to claim 1, wherein the alternating field has a frequency greater than 100 KHz.

3. Measuring apparatus according to claim 1, wherein the circuit device is substantially non-resonant at the measuring frequency of the alternating field which is used, and measurement is based on the propagation of a travelling high-frequency wave in the measuring capacitor.

4. Measuring apparatus according to claim 3, wherein the circuit device determines two measurable variables independent of each other and dependent on the amplitude and/or the phase shift of the high-frequency wave influenced by the product.

5. Measuring apparatus according to claim 3, further comprising a control device to keep constant the amplitude of the high-frequency wave.

6. Measuring apparatus according to claim 1, further comprising a sensor encompassing the measuring capacitor, the sensor comprising a material with a low temperature expansion coefficient.

7. Measuring apparatus according to claim 1, further comprising a sensor encompassing the measuring capacitor and a device for keeping the temperature of the measuring capacitor constant.

8. Measuring apparatus according to claim 1, wherein the measuring capacitor comprises plates arranged substantially perpendicularly to a direction of transport of the product.

9. Measuring apparatus according to claim 1, further comprising a sensor encompassing the measuring capacitor, wherein the measuring capacitor includes electrodes, and the sensor is adapted to feed the product through a space formed between the electrodes.

10. Measuring apparatus according to claim 1, wherein the measuring capacitor includes electrodes, and each electrode has a central product feed through opening.

11. Measuring apparatus according to claim 10, further comprising a tubular, outwardly extending conducting surface located on each electrode, wherein the conducting surfaces surround the product.

12. Measuring apparatus according to claim 1, wherein the measuring capacitor includes electrodes formed by a metal coating.

13. Measuring apparatus according to claim 1, further comprising a sensor encompassing the measuring capacitor, wherein the sensor comprises a non-conducting portion for defining a field-filled space of the measuring capacitor.

14. Measuring apparatus according to claim 1, further comprising a sensor encompassing the measuring capacitor, wherein the sensor has a non-conducting tube directly surrounding the product.

15. Measuring apparatus according to claim 1, wherein the measuring capacitor includes electrodes defining a field filled space, and the field filled space of the measuring capacitor is partially or completely filled with the tobacco, cotton or other fibrous product having a dielectric constant.

16. Measuring apparatus according to claim 1, wherein the circuit device determines a measurable variable dependent on the capacitance of the measuring capacitor.

17. Measuring apparatus according to claim 1, wherein the circuit device determines a measurable variable dependent on the dielectric loss factor of the measuring capacitor.

18. Measuring apparatus according to claim 1, wherein the measuring capacitor forms part of an RC network.

19. Measuring apparatus according to claim 1, wherein the circuit device comprises an inverting operational amplifier.

20. Measuring apparatus according to claim 1, wherein the capacitance of the measuring capacitor is less than 10 pF.

21. Measuring apparatus according to claim 1, wherein the measuring device includes a plurality of measuring capacitors arranged lengthwise across the product.

22. Measuring apparatus according to claim 21, wherein the measuring capacitors include electrodes connected to the high-frequency field generating device, the electrodes being kept at the same potential.

23. Measuring apparatus according to claim 21, further comprising inverting operational amplifiers operating to keep the other electrodes in the measuring capacitors at substantially the same potential.

24. Measuring apparatus according to claim 21, wherein the other electrodes respectively are connected to the circuit device for determining the at least one suitable measurable variable of the high-frequency field influenced by the product.

25. Measuring apparatus for the detection of foreign bodies in a tobacco, cotton or other fibrous product, comprising:

a measuring device, a device for generating an alternating electromagnetic field in the measuring device, which is influenced by a product arranged in a measuring volume of the measuring apparatus, a circuit device which includes the measuring device and which determines at least one suitable measurable variable of the alternating field influenced by the product, and an evaluating device that detects the foreign body by suitable evaluation of the measurable variable determined with the circuit device, wherein the measuring device comprises a measuring capacitor and the frequency of the alternating field is in the high-frequency range below the microwave range, a part of the circuit device which serves to determine the at least one measurable variable comprises digital electronics, the device for determining the measurable variables is designed to sample the measuring signal with a sampling frequency which is higher by a factor of n than the frequency of the high-frequency field, wherein n is a positive integer greater than 1, and the device for determining the measurable variables comprises a digital processing device for separately multiplying n scanned measurements by corresponding sine and cosine values, and for separately adding up these sine and cosine products.

26. Measuring method for the detection of foreign bodies in a tobacco, cotton or other fibrous product, comprising:

generating a measuring device in which an input signal for generating an alternating electromagnetic field in a measuring device comprising a measuring capacitor, wherein the alternating electromagnetic field is in the high frequency range or very high frequency range below the microwave range, and is influenced by a foreign body contained in the product, determining at least one suitable measurable variable of the alternating field influenced by the foreign body using a rectifier receiving an output signal from the measuring capacitor, and a multiplication amplifier receiving the input signal and the output signal, and evaluating the measurable variable for detection of the foreign body.

27. Measuring method according to claim 26, wherein the alternating field has a frequency greater than 100 KHz.

28. Measuring method according to claim 26, further comprising performing the measurement in a non-resonant fashion using a travelling high-frequency wave.

29. Measuring method according to claim 28, further comprising determining at least one measurable variable dependent on the amplitude and/or the phase shift of the high-frequency wave influenced by the foreign body.

30. Measuring method according to claim 28, further comprising sampling the measuring signal with a sampling frequency which is higher by a factor of n than the frequency of the high-frequency wave, wherein n is a positive integer greater than 1.

31. Measuring method for the detection of foreign bodies in a tobacco, cotton or other fibrous product, comprising:
  generating an electromagnetic field in a measuring device, the electromagnetic field being influenced by a foreign body contained in the product;
  determining at least one suitable measurable variable of the alternating field influenced by the foreign body; and
  evaluating the measurable variable for detection of the foreign body,
  wherein the measuring device comprises a measuring capacitor, and an alternating field in the high-frequency range below the microwave range is used, measurement is carried out in non-resonant fashion by means of a traveling high-frequency wave, the measuring signal is sampled with a sampling frequency which is higher by a factor of n than the frequency of the high-frequency wave, wherein n is a positive integer greater than 1, and in each case n sampled measurements are multiplied separately by corresponding sine and cosine values, and these sine and cosine products are added up separately.

32. Measuring apparatus for the detection of foreign bodies in a tobacco, cotton or other fibrous product, comprising:
  a measuring device comprising a measuring capacitor,
  an oscillator generating a clock signal for an alternating electromagnetic field in the measuring device, the alternating electromagnetic field being in the high-frequency range below the microwave range, wherein the alternating electromagnetic field is influenced by a product arranged in a measuring volume of the measuring apparatus,
  a circuit device that determines at least one suitable measurable variable of the alternating field influenced by the product, the circuit device comprising the measuring capacitor, and an A/D converter receiving the clock signal from the oscillator and an output signal from the measuring capacitor, wherein the device for determining the measurable variables samples the measuring signal with a sampling frequency which is higher by a factor of n than the frequency of the high-frequency field, wherein n is a positive integer greater than 1, and
  an evaluating device that detects the foreign body by suitable evaluation of the measurable variable determined with the circuit device.

33. Measuring apparatus according to claim 32, wherein the device for determining the measurable variables samples the measuring signal with a sampling frequency which is higher by a factor of n than the frequency of the high-frequency field.

* * * * *